US00PP21514P2

(12) United States Plant Patent
Horvath

(10) Patent No.: US PP21,514 P2
(45) Date of Patent: Nov. 23, 2010

(54) *GEUM* PLANT NAMED 'TEQUILA SUNRISE'
(50) Latin Name: *Geum hybrid*
Varietal Denomination: Tequila Sunrise

(76) Inventor: Brent Horvath, 10702 Seaman Rd., Fontana, WI (US) 60034

( * ) Notice: Subject to any disclaimer, the term of this patent is extended or adjusted under 35 U.S.C. 154(b) by 5 days.

(21) Appl. No.: 12/291,372

(22) Filed: Nov. 10, 2008

(51) Int. Cl.
*A01H 5/00* (2006.01)

(52) U.S. Cl. ..... Plt./263.1
(58) Field of Classification Search ..... Plt./263.1
See application file for complete search history.

*Primary Examiner*—Annette H Para
*Assistant Examiner*—Louanne C Krawczewicz Myers

(57) ABSTRACT

A new, distinct *Geum* plant as shown and described, characterized by semi double flowers of yellow with rose colored tips.

2 Drawing Sheets

Figure 1:
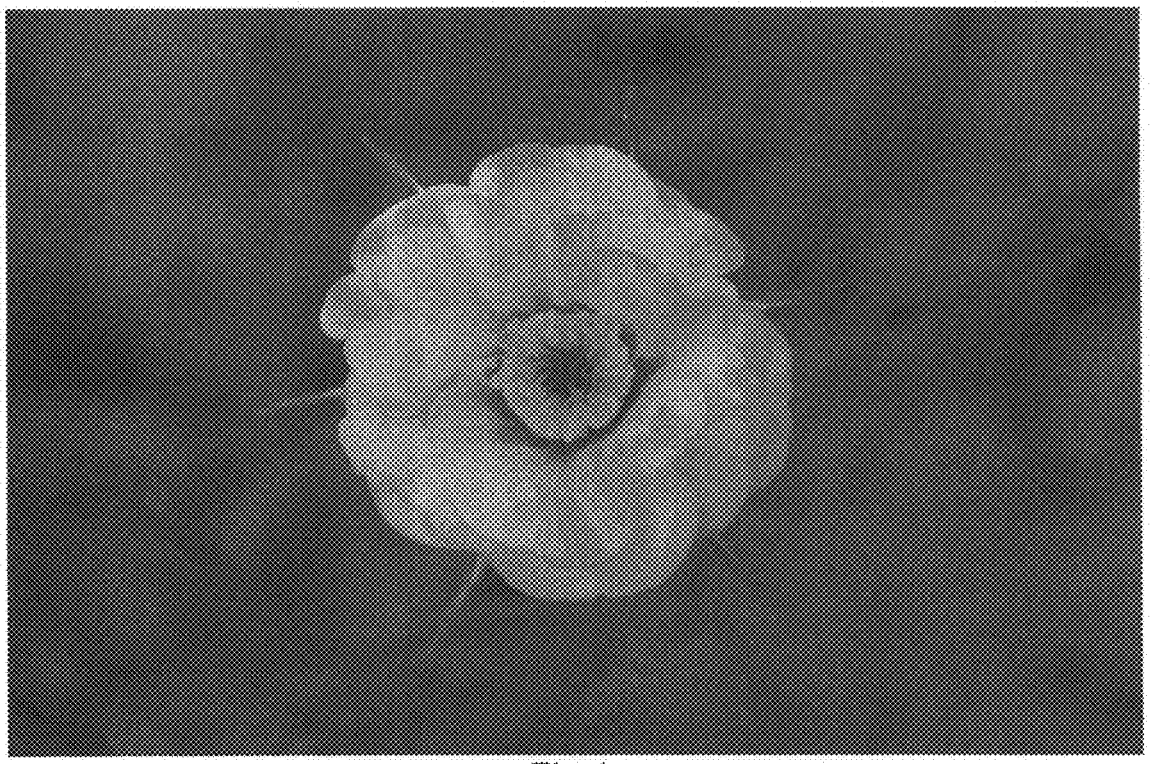

Latin name: *Geum hybrid.*
Cultivar name: 'Tequila Sunrise'.

BACKGROUND OF THE INVENTION

The present invention relates to a new and distinct hybrid of *Geum* plant named 'Tequila Sunrise' characterized by semi double flowers of yellow with rose colored tips. The new *Geum* was raised as a seedling from a controlled cross of *Geum* 'Mango Lassi, not patented, and *Geum* 'Flames of Passion' U.S. Plant Pat. No. 13,730, patented, in Hebron, Ill. in 2005. The selection of the new plant was due to its' combination of yellow and rose colored flowers. Asexual division have been the means of reproduction. Division propagation has taken place at a nursery Hebron, Ill. since 2006. The new *Geum* has shown to be stable and identical in reproduction to the parent after dividing over 30 two year old plants resulting in over 1200 divisions from 2006 to 2008.

SUMMARY OF THE INVENTION

In the following description, color references are made to The Royal Horticultural Society Colour Chart. The new *Geum* plant named 'Tequila Sunrise' characterized by semi double flowers of yellow 9 B with rose colored tips 46 A compared to the parents have been observed to be unique and stable.

Plants of the new *Geum* can be compared to plants of the male or pollen parent *Geum* 'Flames of Passion' U.S. Plant Pat. No. 13,730, patented. 1. The new plant flower colors are yellow RHS 9 B which blends into 46 A while *Geum* 'Flames of Passion' has a red flower color 179 A.

Plants of the new *Geum* can also be compared to the female or seed parent plant *Geum* 'Mango Lassi', not patented. 1. The new plant flower colors are yellow RHS 9 B which blends into 46 A, while *Geum* 'Mango Lassi' has a golden yellow 14 B and orange red 44 A flower color.

DESCRIPTION OF PHOTOGRAPHS

FIG. 1. Close up of the flower.

Figure 2:
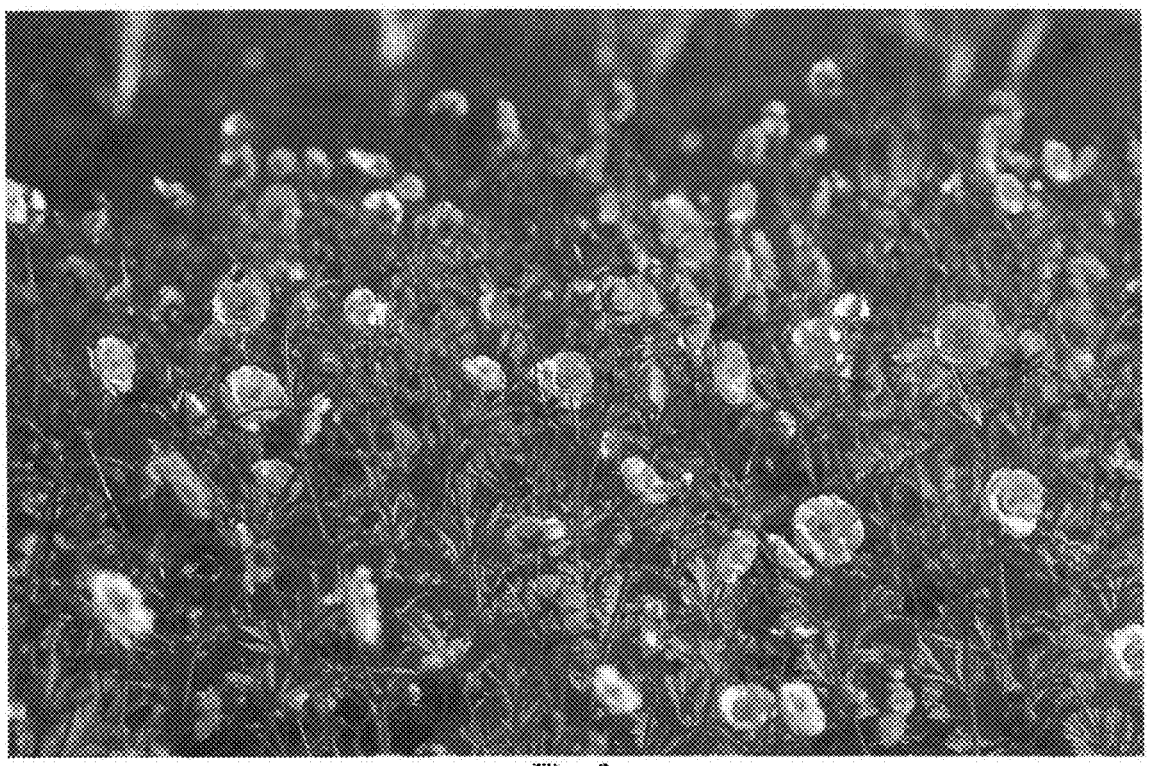

FIG. 2. Blooming plants in May.

Figure 3:
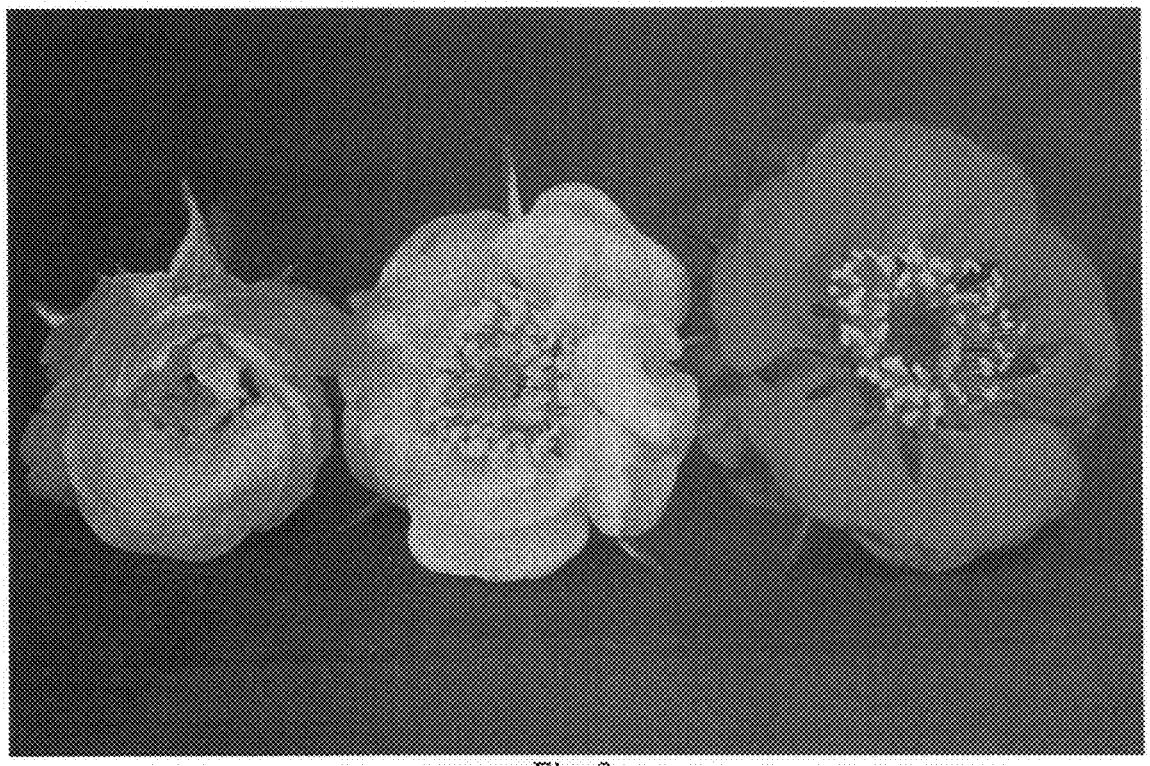

FIG. 3. From left to right, *Geum* 'Mango Lassi', *Geum* 'Tequila Sunrise', *Geum* 'Flames of Passion'. New plant in the middle pictured with parent plants.

DETAILED BOTANICAL DESCRIPTION

In the following description, color references are made to The Royal Horticultural Society Colour Chart. Plants used for the description were grown in a field for two years at a nursery in Hebron, Ill. Measurements and numerical values represent averages of typical plants.

Botanical classification: *Geum* hybrid cultivar Tequila Sunrise.

Parentage: Male or pollen *Geum* 'Flames of Passion' U.S. Plant Pat. No. 13,730 and female or seed *Geum* 'Mango Lassi'.

Propagation: Vegetative division.

Plant Description: Overall habit of the new *Geum* is basal clumps, upright flower stems topped by semi double flowers of yellow RHS color 9 B which blends into rose color 46 A.

*Plant height.*—35 cm.
*Plant width.*—35 cm.
*Stem: diameter.*—3 mm.
*Stem or basal branches.*—length 35 cm, with the internode between basal foliage and first leaflet length being 20-25 cm and the second internode between the first leaflet and the second leaflet length being 8-10 cm.
*Stem coloration.*—Of the base of the stem is close to 143 C, coloration of the top of the stem is 59A.

Foliage description:
*Type.*—Deciduous.
*Arrangement.*—Basal alternate with typically two lateral leaflets on the stem.
*Petiole.*—8-10 cm long, with a diameter of 5 mm, and color is 144 D.
*Terminal compound leaf length.*—up to 21 cm.
*Terminal compound leaf width.*—7+ cm.
*Terminal leaflet length.*—Typically 5 cm.
*Terminal leaflet width.*—Typically 35 mm.
*Terminal leaflet shape.*—Obovate with incised margins.
*Terminal and lateral leaf apex.*—Acute.
*Terminal and lateral leaf base.*—Cuneate.
*Terminal and lateral leaf margin.*—Incised.
*Texture.*—Terminal and lateral leaf, upper and lower surfaces: pubescent.
*Venation pattern.*—Terminal and lateral leaf, upper and lower surfaces: pinnate.

*Venation color.*—Terminal and lateral leaf, upper surface is color 137 A and lower surface color is 138 B.
*Lateral leaflet number.*—2 per stem.
*Lateral leaflet length.*—1-2 cm.
*Lateral leaflet width.*—Up to 10 mm.
*Lateral leaflet shape.*—Obovate.
*Adaxial leaf description.*—Color is 146 A.
*Abaxial leaf description.*—Color. 138 B.

Flower description:

*Flower type.*—Solitary.
*Flower color.*—9 B blending into 46 A.
*Flower size.*—Diameter: 25-30mm across, depth 10-15 mm.
*Flower number.*—5 per stem, 150 per plant.
*Number flowering stems.*—30.
*Bloom period and duration.*—Beginning May into June in Hebron, Ill.
*Flower longevity and duration on the plant.*—Approximately 3 weeks.
*Flower longevity and duration cut.*—Not measured.
*Scent.*—None.
*Petal count.*—12-14.
*Petal shape.*—Spatulate.
*Petal arrangement.*—Rotate, overlapping.
*Petal diameter or width.*—12 mm across and petal length—10 mm long.
*Petal apex.*—Retuse, base: attenuate, margin: entire.
*Petal texture.*—Upper and lower surfaces: smooth, glabrous.
*Petal color.*—Upper surface is color 9 B blending into 46 A.
*Petal color.*—Lower surface color was not measured.
*Inflorescence diameter and height.*—8-12 cm across, 10 cm long.
*Flower buds.*—Diameter: 10-12mm across, depth: 1 cm, shape: ovoid, surface: slightly pubescent and color 59 A.
*Sepal size.*—Length: 11-13 mm long, diameter: 6 mm at base coming to a point
*Sepal quantity.*—Six.
*Sepal shape.*—Lanceolate, apex: acute, base: cuneate, margin: entire.
*Sepal texture.*—Upper and lower surfaces: Pubescent.
*Sepal color.*—Adaxial color green 146 D, Abaxial color 59 A.
*Peduncle color.*—Purple N 77 A.
*Peduncle size.*—Length: 20-25 cm, diameter: 3 mm.
*Pedicel size.*—Length: 8-10 cm, diameter: 1-2 mm and color 59 A.
*Reproductive organs.*—Stamen — quantity over 100, length 1 cm.
*Anther.*—Quantity: over 100, length: 1 mm, diameter: close to 0.5 mm.
*Pollen.*—Typically present, color: almost 5 A.
*Stigma.*—None observed.
*Style.*—Length: 6 mm, number: over 50.
*Pistil.*—Number: over 50, length: 6+ mm.
*Ovaries.*—None observed.
*Fruit.*—None observed.

Disease resistance: Resistance to diseases common to *Geum* has not been observed on plants grown under nursery conditions.

I claim:

1. A new, distinct *Geum* plant as shown and described, characterized by semi double flowers of yellow with rose colored tips.

* * * * *